United States Patent [19]

Nishinaka et al.

[11] Patent Number: 4,740,469
[45] Date of Patent: Apr. 26, 1988

[54] ENZYME-GRANULATING METHOD AND GRANULAR COMPOSITION CONTAINING ENZYME

[75] Inventors: Masayuki Nishinaka; Hitoshi Iijima, both of Kanagawa, Japan

[73] Assignee: Showa Denko Kabushiki Kaisha, Tokyo, Japan

[21] Appl. No.: 787,590

[22] Filed: Oct. 15, 1985

[30] Foreign Application Priority Data

Oct. 12, 1984 [JP] Japan ................................. 59-213669

[51] Int. Cl.$^4$ ........................... C12N 9/98; C12R 1/07; C11D 3/386
[52] U.S. Cl. ..................... 435/187; 435/832; 252/174.12
[58] Field of Search .................. 435/187, 180, 182; 252/174.12

[56] References Cited

U.S. PATENT DOCUMENTS 4,106,991 8/1978 Markussen et al. ................. 435/187
4,572,897 2/1986 Amotz et al. ....................... 435/177

FOREIGN PATENT DOCUMENTS 57-165497 10/1982 Japan ................................... 435/187

Primary Examiner—Lionel M. Shapiro
Attorney, Agent, or Firm—Sughrue, Mion, Zinn, Macpeak, and Seas

[57] ABSTRACT

A method for granulating an enzyme is disclosed, which comprises supplying a granulator with a feed composition consisting essentially of from 1 to 35% by weight of an enzyme and from 0.5 to 30% by weight of a synthetic fiber chip or pulp, with the balance being an extender or filler, shaping the supplied feed composition into granules and drying said granules. A granulated enzyme product thereof is also disclosed, having an improved stability and enhanced strength, as well as a high degree of disintegratability in washing water.

16 Claims, No Drawings

ENZYME-GRANULATING METHOD AND GRANULAR COMPOSITION CONTAINING ENZYME

FIELD OF THE INVENTION

The present invention relates to a method for granulating an enzyme and a granulated enzyme product thereof.

BACKGROUND OF THE INVENTION

Granulated enzyme products are extensively used in the detergent, food, medical, leather and textile industries, as well as in the production of processed marine products, and a variety of commercial products suitable for specific purposes are available.

A granulated enzyme has the following advantages over an enzyme powder: (1) high flowability, (2) ease of measuring, (3) no sticking to the walls of a container, (4) no formation of agglomerates, (5) improved appearance, and (6) high stability. If a granulated enzyme is used in a medicine or detergent, it must meet additional requirements such that it should easily disintegrate in liquids and have sufficient strength to withstand the usual handling of granules.

Conventional enzyme granules are produced by charging a mixture of an enzyme powder and water into a granulator, and granulating the powder either in the presence or in the absence of a binder etc. During the granulation, the charged mixture will stick to the walls of the granulator, and the resulting deposit is not only undesirable from a hygienic viewpoint but it also causes problems in the carrying out of the granulation of the powder smoothly. A method of avoiding this problem, by using a properly adjusted amount of water, is effective only in a limited range, and it often occurs that granules grow too fast to enable precise control over the granule size.

It is known that fibrous cellulose is used as an ingredient for a granular composition containing an enzyme to improve granulation characteristics, as described in U.S. Pat. No. 4,106,991. However, the resulting granular composition is still fragile and insufficient in toughness against fracture. Further, as the content of enzyme in the granular composition is increased, it becomes more difficult to avoid sticking of the charged mixture to the walls of the granulator, and therefore it is necessary to add a very large amount of fibrous cellulose in the composition in order to minimize sticking.

SUMMARY OF THE INVENTION

One object of the present invention is to provide a granular composition containing an enzyme, particularly one suitable for use in detergents, the granular composition (hereinafter sometimes referred to as "enzyme granules") not only having an improved stability and enhanced strength, but also exhibiting a high degree of disintegratability in washing water.

Another object of the invention is to provide a method for granulating an enzyme that solves all the problems associated with the use of an enzyme in conventional detergents, and which is capable of producing enzyme granules that are attractive uniform in size, and highly flowable.

A further object of the present invention is to provide a process for preparing enzyme granules that ensures a smooth granulating operation without sticking on the walls of the granulator, and which is capable of producing stabilized enzyme granules with a uniform size that may be provided with an attractive color if desired.

In accordance with the present invention, a composition consisting essentially of from 1 to 35% by weight of an enzyme and from 0.5 to 30% by weight of synthetic fiber chip or pulp, with the balance being an extender or filler, is supplied to a granulator, and the composition is shaped into granules and dried.

DETAILED DESCRIPTION OF THE INVENTION

Enzymes which can be used in the present invention include those commonly used in the detergent and other aforementioned industries, such as amylase, lipase, protease and cellulase, but the present invention is not limited thereto and any enzymes derived from microorganisms, for example, Genus Bacillus, Streptomyces, and Aspergillus can be used. The enzyme may be used either in a dry form or as an aqueous solution. They may be used alone or in combination. The amount of enzyme is from 1 to 35% by weight and preferably from 4 to 20% by weight. An alkaline protease API-21, derived from genus Bacillus sp.nov. NKS-21 which is described in U.S. Pat. No. 4,480,037 and which has been deposited since Feb. 3, 1982 in the Fermentation Research Institute (FERI) in Japan as Bacillus sp. FERM BP-93, is an example of the protease.

In accordance with the present invention, enzyme granules of improved strength and disintegratability can be obtained by granulating an enzyme together with a fine synthetic fibrous material in a form of chip or pulp. One particular advantage of synthetic fibers is that they provide good lubricity during the working in a granulator, and therefore they are dispersed sufficiently to provide efficient granulation and produce enzyme granules of a satisfactory strength and a good disintegratability.

Preferred examples of synthetic fibers include Nylon, polyethylene, polypropylene, vinylon, polyester and acrylic fibers, which have an average fiber length of from 100 to 500 $\mu$m and a fiber finenesse of from 0.05 to 0.7 denier, preferably from 0.3 to 0.5 denier. The synthetic fiber is incorporated in an amount of from 0.5 to 30% by weight and preferably from 2 to 20% by weight Vinylon fibers with a fineness of 0.53 denier can be chopped to a fiber length of 0.3 mm by a dry cutting method, and such chopped vinylon fibers of fiber lengths of from 0.3 to 0.5 mm are preferably used in the present invention.

The remainder of the composition is an extender or filler. Extenders or fillers suitable for use in the present invention include water-soluble or -dispersible inorganic salts of alkali metals and alkaline earth metals such as Na, K, Mg and Ca. For example, sodium sulfate, sodium chloride, calcium sulfate and calcium carbonate are used as extenders or fillers for enzyme granules suitable for detergent compositions.

The composition of the present invention may further contain a suitable additive such as binder, granulation aid, colorant, stabilizer or reinforcing agent, which are conventionally used in the fields of granulation and enzyme preparations. For instance, the feed composition preferably includes at least two of binder, granulation aid, reinforcing agent and colorant.

Preferred binders are viscous hydrophilic materials commonly used in the field of granulation, and they include polyvinylpyrrolidone, polyvinylalcohol, and cellulose derivatives such as hydroxypropyl cellulose, methyl cellulose and carboxymethyl cellulose (CMC). These binders are generally introduced in the composition as aqueous solutions, but, if desired, binders may be replaced by the sole use of water.

A granulation aid suitable for use in the present invention can be water, or any of the waxy materials that have melting points in the range of from 30° to 70° C. and which are used either as aqueous solutions or dispersions, or in a molten state. The granulation aid is optionally incorporated in an amount as necessary to have good granulation performance and preferably of from 8 to 18% by weight based on the weight of the composition of the present invention. Typical granulation aids include polyethylene glycol, ethoxylated aliphatic alcohol, polyethylene glycol monooleate, and aliphatic acid monoethanolamide. Water and/or waxy materials are used as granulation aids, and they contribute to the formation of granules whether they are used alone or in combination.

Colorants suitable for use in the present invention can be any pigments. For example, $TiO_2$ and/or $CaCO_3$ optionally with $SiO_2$ are used as colorants for enzyme granules suitable for detergent compositions.

In the present invention, a mechanical stirring mixer, mixer-type granulator, drum granulator and any other types of granulators may be used, with those mixer blades and/or chopper blades being preferred.

The granulation is generally carried out at a temperature of from 10° to 50° C., preferably from 25° to 40° C., and the components of the feed composition may be supplied into the granulator in any order. Typically, the dry components such as enzyme, synthetic fiber and extender/filler are supplied first, and then optional liquid binder and/or granulation aid (i.e., water and/or waxy material) is sprayed into the granulator through a nozzle. Subsequently the enzyme granules obtained by this procedure are dried in a dryer such as fluidized bed dryer. The dried granules usually have diameters in the range of from 0.1 to 2 mm.

By the method of the present invention, smooth-surfaced enzyme granules can be efficiently obtained without any sticking or composition of the feed composition on the walls of the granulator, and this effect is assumed to result largely from the use of synthetic fiber chip or pulp.

The use of synthetic fiber chip or pulp also contributes to the formation of enzyme granules which have good shape retention and wear-resistant properties, so that the method of the invention can be implemented to reduce the formation of dust particles and the occurrence of fractured granules to very low levels. In addition, the synthetic fiber chip or pulp swells by absorbing water, and thus provides enzyme granules having good disintegratability.

According to one preferred embodiment of the present invention, the dried granules obtained by the aforementioned procedure are supplied into a heated mixer at a temperature of from 20° to 120° C., preferably from 50° to 80° C., and then a meltable waxy material such as polyethylene glycol is supplied and mixed with the granules, so that the granules are smoothly coated with the molten wax. Further a finely divided colorant comprising $TiO_2$ and/or $CaCO_3$, optionally with $SiO_2$, is supplied into the mixer and mixed with the granules and thereafter the coated and colored granules thus obtained are cooled if necessary, whereby enzyme granules having smoothly coated and white-colored surfaces which prevent dust formation from the granules can be obtained.

The following examples are provided to further illustrate the present invention, but should not be taken as limiting the scope of the invention.

EXAMPLE 1

A granulator (LMA-10 of Nara Kikai K.K.) was supplied with 1,080 g of ground sodium sulfate, 330 g of protease powder (API-21), 60 g of vinylon chips (0.53 denier in fineness and 0.3 mm in length) and 30 g of titanium dioxide, and the components supplied were mixed together by mixer blades and chopper rotary blades rotating at 200 rpm and 3,000 rpm, respectively, for 3 minutes.

While the mixer blades and chopper blades were rotating at the speeds indicated above, 200 g of a 1% aqueous CMC solution was sprayed into the granulator through a air-atmizing nozzle, and the mixing of the components was continued for an additional 12 minutes with the rotational speed of the mixer blades increased to 350 rpm. As a result, enzyme granules which are from spherical to ellipsoidal in shape and of a narrow size distribution were obtained.

The granules were fed into a fluidized bed dryer where they were dried to a water content of 3% or less.

The dried granules had the following size (average diameter) distribution:

| | |
|---|---|
| Over 1.4 mm | 13.6% |
| From 0.35 to 1.4 mm | 86.2% |
| Under 0.35 mm | 0.2% |

COMPARATIVE EXAMPLE 1

The procedure of Example 1 was repeated, except that no fiber chips were used. The resulting granules had very uneven surfaces and were accompanied by the extensive formation of fines.

Details of Comparative Example 1 are as follows. A granulator (Model LMA-10 of Nara Kikai K.K.) was charged with 1,050 g of ground sodium sulfate, 340 g of protease powder (API-21), and 30 g of titanium dioxide, and the components supplied were mixed together by mixer blades and chopper rotary blades rotating at 200 rpm and 3,000 rpm, respectively, for 3 minutes. While the mixing was continued under the same conditions, a 1% aqueous CMC solution was sprayed into the granulator through a air-atmizing nozzle, and the mixture was subjected to a 10-minute agitation.

Thereafter, the mixing was continued for an additional 12 minutes with the mixer blades rotating at 350 rpm.

The resulting granules were ellipsoids with uneven surfaces. They were fed into a fluidized bed dryer where they were dried to a water content of 3% or less. The dried granules had the following size distribution:

| | |
|---|---|
| Over 1.4 mm | 19.0% |
| From 0.35 to 1.4 mm | 58.0% |
| Under 0.35 mm | 23.0% |

EXAMPLE 2

The procedure of Example 1 was repeated, except that the granulator was supplied with 1,440 g of ground sodium sulfate, 440 g of enzyme powder (API-21), 80 g of vinylon chips (0.53 denier in fineness and 0.3 mm in length), and 40 g of titanium dioxide. The resulting enzyme granules wer from spherical to ellipsoidal in shape and from light gray to white in color, and they had smooth surfaces without fiber projections.

EXAMPLE 3

The procedure of Example 1 was repeated, except that the granulator was supplied with 1,520 g of ground sodium sulfate, 360 g of enzyme powder (API-21), 80 g of vinylon chips (0.53 denier in fineness and 0.3 mm in length), and 40 g of titanium dioxide.

EXAMPLE 4

The procedure of Example 1 was repeated, except that the granulator was supplied with 1,200 g of ground sodium sulfate, 360 g of enzyme powder (API-21), 400 g of synthetic pulp (polyethylene fibers with an average diameter of 50 μm and length of 0.1 mm), and 40 g of titanium dioxide.

COMPARATIVE EXAMPLE 2

The procedure of Example 1 was repeated, except that the granulator was supplied with 1,400 g of ground sodium sulfate, 360 g of enzyme powder (API-21), 200 g of cellulose fibers (average diameter of 30 μm and length of 0.15 mm), and 40 g of titanium dioxide.

Fracture Test

Each of the granular enzyme samples prepared in Examples 3 and 4, and Comparative Examples 1 and 2 was passed through two Tyler sieves (12 mesh and 48 mesh) to obtain granules of sizes in the range of from 0.3 to 1.4 mm. Two hundred grams of each of the sieved enzyme samples was charged into a stainless steel ball mill (ID: 100 mm, L: 150 mm) together with 200 g of steel balls (0.25 inch in diameter), and was ground at 100 rpm for 30 minutes. Each of the ground samples was recovered from the ball mill and passed through two Tyler sieves (12 mesh and 48 mesh), and the portion that passed through the 48-mesh sieve was collected. The strength of each enzyme sample was determined by calculating the percentage of granules fractured ($\alpha$) in the ball milled samples as follows:

$$\text{Percentage of granules fractured } \alpha \text{ in ball mill} = \frac{W}{200} \times 100\ (\%),$$

wherein W is the weight in grams of the granules passing through the 48-mesh sieve.

The data obtained are shown below.

| | Percantages of granules fractured in ball mill ($\alpha$) | |
|---|---|---|
| Example 3 | Vinylon chips | 2.4% |
| Example 4 | Synthetic pulp (polyethylene) | 6% |
| Comparative Example 1 | Cellulose fibers | 10% |
| Example 2 Comparative Example 1 | No fibers | 65% |

While the invention has been described in detail and with reference to specific embodiments thereof, it will be apparent to one skilled in the art that various changes and modifications can be made therein without departing from the spirit and scope thereof.

What is claimed is:

1. A method for granulating an enzyme, which comprises supplying a granulator with a feed composition consisting essentially of from 1 to 35% by weight of an enzyme and from 0.5 to 30% by weight of a synthetic fibrous material having an average length in the range of from 100 to 500 μm and a fineness in thr range of from 0.05 to 0.7 denier, with the balance being an extender or filler, shaping the supplied feed composition into granules and drying said granules.

2. A method according to claim 1, wherein said enzyme is selected from the group consisting of amylase, lipase, protease and cellulase.

3. A method according to claim 2, wherein said enzyme is a protease.

4. A method according to claim 3, wherein said protease is API-21 derived from genus Bacillus.

5. A method according to claim 1, wherein said granules are further coated with a molten waxy material.

6. A method according to claim 5, wherein said coated granules are further coated with a finely divided colorant.

7. A method according to claim 6, wherein said colorant is $TiO_2$.

8. A method according to claim 5, wherein said molten waxy material is polyethylene glycol.

9. A granular composition consisting essentially of from 1 to 35% by weight of an enzyme and from 0.5 to 30% by weight of a synthetic fibrous material having an average length in the range of from 100 to 500 μm and a fineness in the range of from 0.05 to 0.7 denier, with the balance being an extender or filler.

10. A granular composition according to claim 9, wherein said enzyme is selected from the group consisting of amylase, lipase, protease and cellulase.

11. A granular composition according to claim 10, wherein said enzyme is a protease.

12. A granular composition according to claim 11, wherein said protease is API-21 derived from genus Bacillus.

13. A granular composition according to claim 9, wherein said granular composition is further coated with a molten waxy material.

14. A granular composition according to claim 13, wherein said coated granular composition is further coated with a finely divided colorant.

15. A granule composition according to claim 14, wherein said colorant is $TiO_2$.

16. A granular composition according to claim 13, wherein said molten waxy material is polyethylene glycol.

* * * * *